United States Patent
Howell et al.

(10) Patent No.: US 6,228,062 B1
(45) Date of Patent: May 8, 2001

(54) ONE PIECE LOCK FOR SPLITTABLE SHEATH

(75) Inventors: Glade H. Howell, Sandy; Weston Finch Harding, Lehi; Steven Wayne Johnson, West Jordan; Christopher Noel Cindrich, South Jordan; Carolyn Elizabeth Brown, Salt Lake City, all of UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/153,340

(22) Filed: Sep. 15, 1998

(51) Int. Cl.[7] ................................................. A61M 5/00
(52) U.S. Cl. ................................ 604/171; 604/165.01
(58) Field of Search .......................... 604/171, 163–165, 604/160, 158, 506, 117, 172, 263, 264, 162, 198, 177, 500, 523

(56) References Cited

U.S. PATENT DOCUMENTS

| 2,503,327 | | 4/1950 | Fields . | |
| 3,167,072 | * | 1/1965 | Stone et al. . | |
| 3,786,810 | | 1/1974 | Pannier, Jr. et al. . | |
| 4,307,869 | | 12/1981 | Mittleman . | |
| 4,349,022 | | 9/1982 | Ishikawa . | |
| 4,801,294 | * | 1/1989 | Okada | 604/171 |
| 4,840,613 | | 6/1989 | Balbierz | 604/533 |
| 5,829,430 | * | 11/1998 | Islava | 128/200.26 |
| 5,843,051 | * | 12/1998 | Adams et al. | 604/525 |

FOREIGN PATENT DOCUMENTS 0 821 980   2/1998   (EP) .

* cited by examiner

Primary Examiner—Richard K. Seidel
Assistant Examiner—Jeremy Thissell
(74) Attorney, Agent, or Firm—Eric M. Lee, Esq.

(57) ABSTRACT

A sheath lock for use with a splittable sheath is disclosed. The sheath lock includes a tapered slot extending from a wide untapered end to a narrow tapered end. A lock box is located adjacent the narrow tapered end of the tapered slot. The lock box has a plurality of tines which grip and retain the sheath when it is positioned within the lock box. The sheath can freely move through the wide untapered end, but the sheath is securely locked when it is moved through the tapered slot from the untapered end into the lock box. The plurality of tines can be arranged in various configurations to form the lock box, including elliptical, circular, rectangular or square configurations around the lock box.

13 Claims, 4 Drawing Sheets

ONE PIECE LOCK FOR SPLITTABLE SHEATH

FIELD OF THE INVENTION

The present invention relates to a sheath lock device. More particularly, the present invention relates to a one piece sheath lock of the type used with a catheter insertion assembly which uses a splittable sheath to advance a catheter within a patient and in which the sheath lock secures the sheath and maintains the desired catheter insertion length.

BACKGROUND

There are countless devices for introducing a catheter within a patient for infusion or extraction of fluids. One class of such devices includes a catheter assembly having a catheter, which can be of an extended length, an insertion needle and a winged catheter inserter. As with conventional catheter placement kits, the insertion needle is positioned within the interior of the catheter, with the tip of the needle extending out of the tip of the catheter. In such a device, the proximal end of the catheter usually terminates at a hub. A wire is attached to the needle and threaded through the interior of the catheter. The wire terminates at a knob which is removably attached to the hub.

Near the distal end of the catheter and needle is an inserter. The inserter is commonly an inserter having a wing structure similar to that widely used in the catheter art. Disposed through the center of the inserter is a guide channel. The catheter and needle are placed within the interior of the guide channel and pass through the interior of the inserter.

A sheath is placed around the exterior of the catheter over the length of the catheter running from near the inserter to the hub. The sheath is splittable. For instance, the sheath is weakened or has a partial slit along its longitudinal axis. During operation, as the sheath is pulled forward, the catheter within the sheath is also moved forward. This allows the catheter to be inserted into a patient by simply pulling the sheath forward. At the same time, the sheath is opened along its slit and removed from the cannula by sheath stripping means located distal of the inserter structure. Thus, the sheath is split and removed from about the cannula prior to the time the cannula travels through the inserter and into the patient.

A problem faced with catheter assemblies using a splittable sheath is how to securely lock the sheath once the catheter has been properly positioned within the patient. One known device for locking a splittable sheath is disclosed in U.S. Pat. No. 4,840,613 to Balbierz. This patent discloses a two-piece locking mechanism. The locking mechanism includes a first locking member carried by the inserter and a slidable second locking member located about the sheath between the inserter and the hub. The first and second lock members are interlockable with one another. The locking mechanism is used to secure the sheath and catheter in place once they are advanced to the desired location.

The first and second lock members are manufactured with sufficiently close tolerances such that when locked together, they sandwich or compress the sheath within their joined structure to restrict movement of the sheath.

It would be an advancement in the art to provide a simple, yet effective sheath lock which allows the sheath to be easily pulled to properly position the catheter and also allows the sheath to be securely locked into any such desired position.

Such a sheath lock is disclosed and claimed herein.

SUMMARY OF THE INVENTION

The present invention is directed to a sheath lock for use with a splittable sheath. The sheath lock apparatus includes a tapered slot extending from a wide untapered end to a narrow tapered end. A lock box is located adjacent the narrow tapered end of the tapered slot. The lock box preferably has a plurality of tines which grip and retain the sheath when it is positioned within the lock box.

In use, the sheath passes through the tapered slot. The sheath can freely move when located at the wide untapered end, but the sheath is securely locked when it moved through the tapered slot from the untapered end into the lock box.

In a preferred embodiment, the tapered slot is formed from two tapered wall sections which, at the narrow tapered end, form two tines projecting into the lock box. The lock box can include additional tines projecting into the lock box to provide enhanced gripping power for the sheath. The tines can be arranged in various configurations to form the lock box. For instance, the tines can be arranged in an elliptical or circular configuration around the lock box. Alternatively, the plurality of tines can be arranged in a rectangular or square configuration around the lock box.

In a currently preferred embodiment, the sheath lock is used with a catheter introducer assembly having a catheter configured to be inserted into a blood vessel and a catheter introducer configured to introduce the catheter into the blood vessel. A splittable sheath surrounds the catheter from its proximal end to the catheter introducer. The proximal end of the catheter and sheath are attached, such that movement of the sheath causes movement of the catheter. A sheath splitter, disposed adjacent the catheter introducer, is configured to split the sheath and to separate the sheath from the catheter, such that the distal ends of the sheath and catheter are separate. With the distal ends of the sheath and catheter separated, and with the proximal ends of the sheath and catheter attached, the distal end of the catheter can be advanced into the patient's blood vessel by pulling the distal end of the sheath. After the catheter is advanced to a desired location within the patient's blood vessel, the sheath is locked by moving it through the tapered slot from the untapered end into the lock box.

DESCRIPTION OF THE INVENTION

Figure 1:
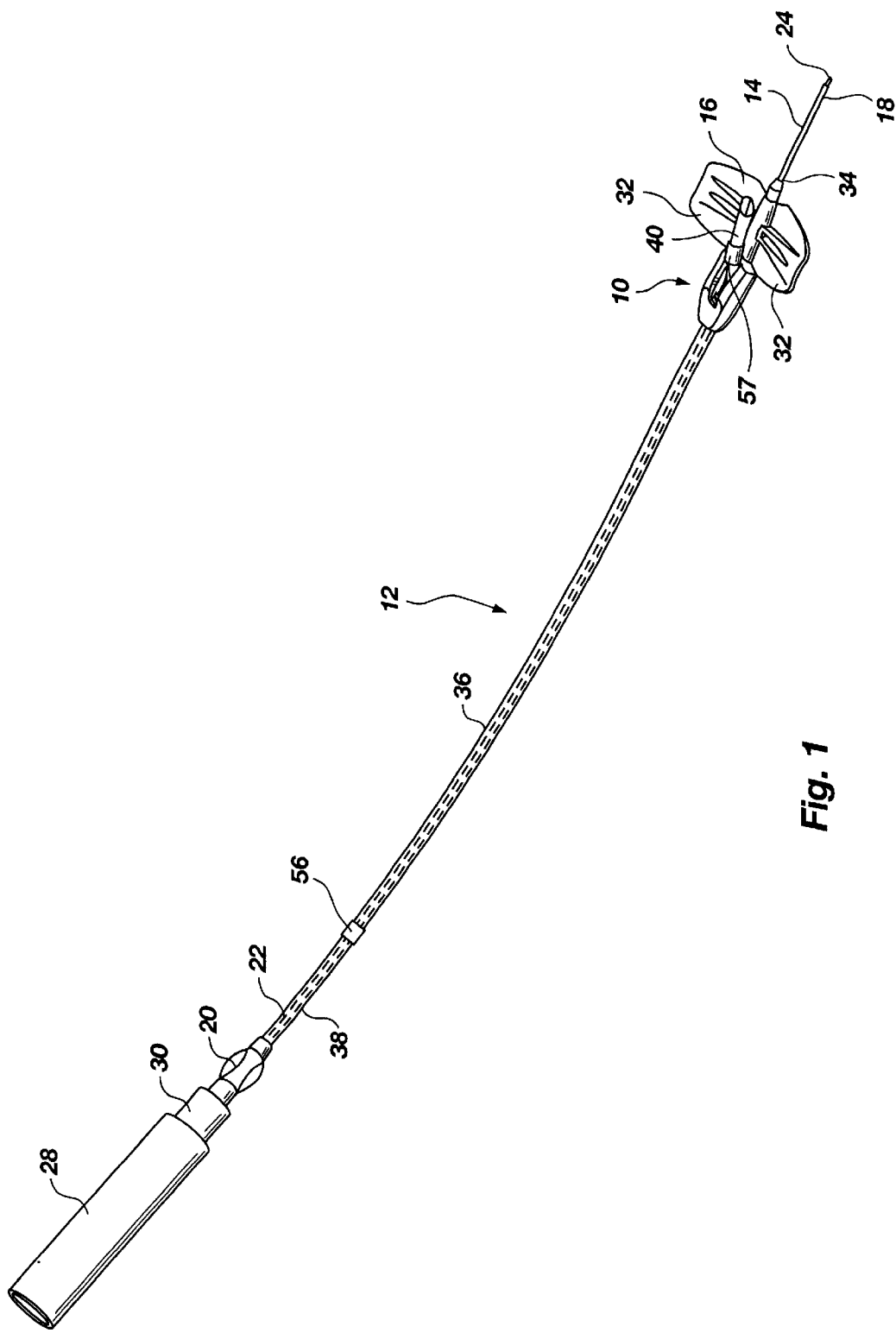
FIG. 1 is a perspective view of a sheath lock within the scope of the present invention used in connection with a winged catheter introducer assembly.

The present invention will now be described with reference to the figures. FIG. 1 shows a sheath lock 10 within the scope of the present invention associated with a winged catheter introducer assembly 12. The catheter introducer assembly is configured for placement of an elongated catheter 14 in the vascular system of a patient. The device also includes a catheter inserter 16 near the distal end 18 of the catheter 14 and a hub 20 near the proximal end 22 of the catheter. A needle 24 is placed within the interior of the catheter. The needle 24 is initially positioned such that the tip of the needle protrudes from the distal end 18 of the catheter 14.

The needle 24 is preferably attached to a wire (not shown). The wire is placed within the interior of the catheter and is attached at the proximal end of the device to a handle 28, which can take a variety of forms. Once the needle 24 has been used to insert the catheter 14 within a patient, the needle 24 is completely removed from the device by pulling on the handle 28, which in turns pulls on the wire attached to the needle 24. In this manner the needle 24 is moved in a proximal direction through the catheter 14, and ultimately exits the proximal end of the device. The catheter introducer assembly 12 may also include a needle receptacle 30 attached near the proximal end of the device. The receptacle 30 is configured in such a manner that the needle 24 is received within the receptacle 30 as it is pulled out of the catheter 14.

The hub 20 is configured such that it can be attached to a fluid line once the catheter 14 is in place within a patient. The hub 20 preferably includes a luer lock mechanism or other type of threaded attachment mechanism such as those known and used in the art. The device may also include a plug (not shown) disposed between the hub and the needle receptacle. The plug has an opening which allows the needle and wire to travel through, yet prevents flow of fluids out of the catheter. Using the plug, it is possible to ready the catheter and a fluid source, such as IV fluid, for attachment without experiencing uncontrolled flow out of the catheter.

The catheter inserter 16, located near the distal end of the winged catheter introducer assembly 12, preferably has wings 32 of the type generally used in the art. The inserter 16 includes a channel 34 through its center which is wide enough that the catheter 14 can pass through. When the wings 32 of the device are pinched together, the catheter 14 and needle 24 within the interior of the channel 34 are securely held in place. When the wings 32 are released, the catheter 14 and needle 24 can be moved through the interior of the channel 34.

The winged catheter introducer assembly 12 preferably includes a splittable sheath 36 which surrounds the catheter 14 from the hub 20 to the sheath lock 10. The proximal end 38 of the sheath 36 is preferably connected to the catheter proximal end 22, for instance, at the hub 20. The distal end 40 of the sheath 36 passes through the sheath lock 10.

Figure 2:
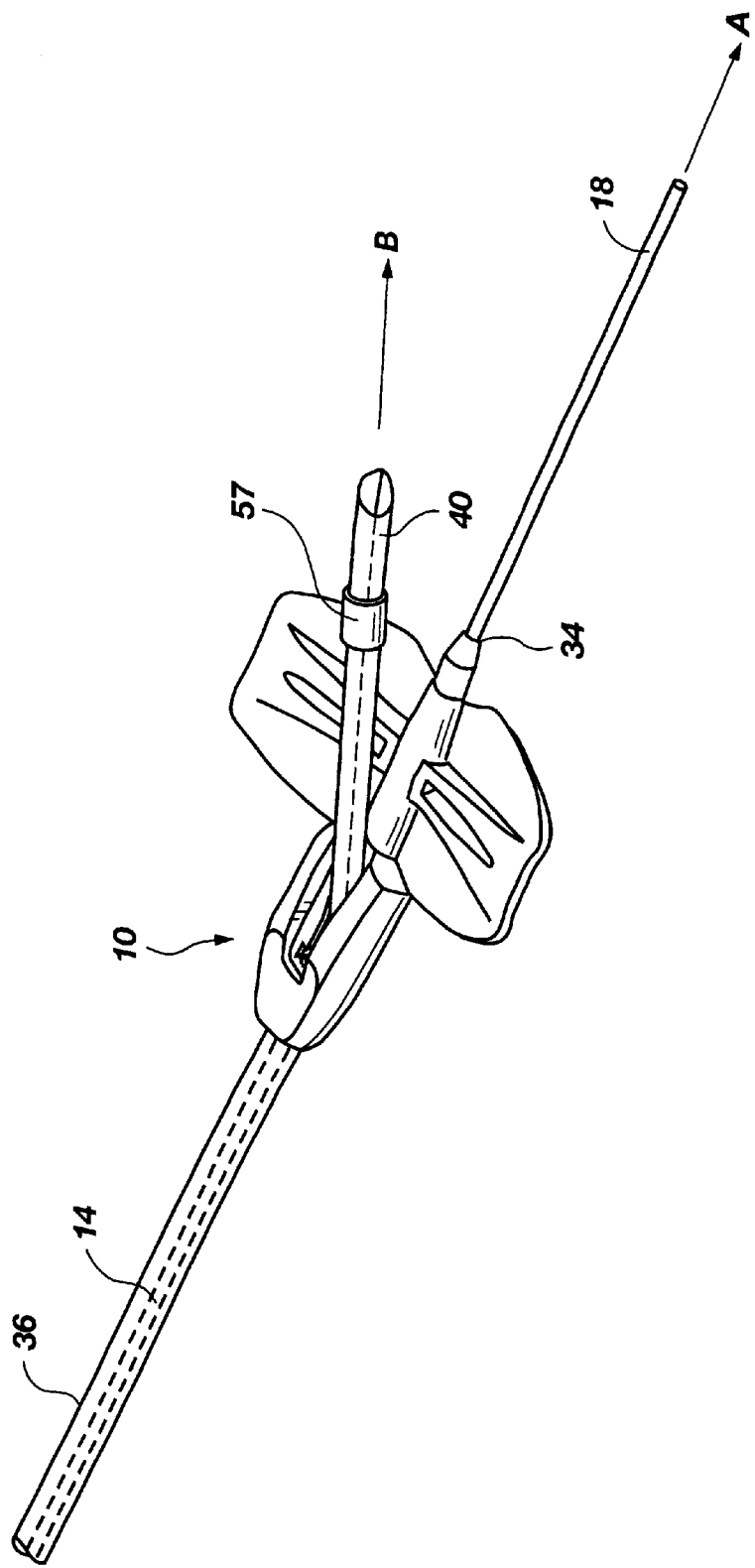
FIG. 2 is an enlarged perspective view of a sheath lock within the scope of the present invention showing that advancing the sheath causes the catheter to also be advanced.

As illustrated in FIG. 2, the catheter distal end 18 is advanced into the patient's blood vessel (shown by Arrow A) by pulling on the sheath distal end 40 (shown by Arrow B). As the sheath 36 passes through the sheath lock 10, it is split and removed from around the catheter 14. In this manner the catheter 14 can be inserted into a patient in a controlled and sterile manner.

Figure 3:
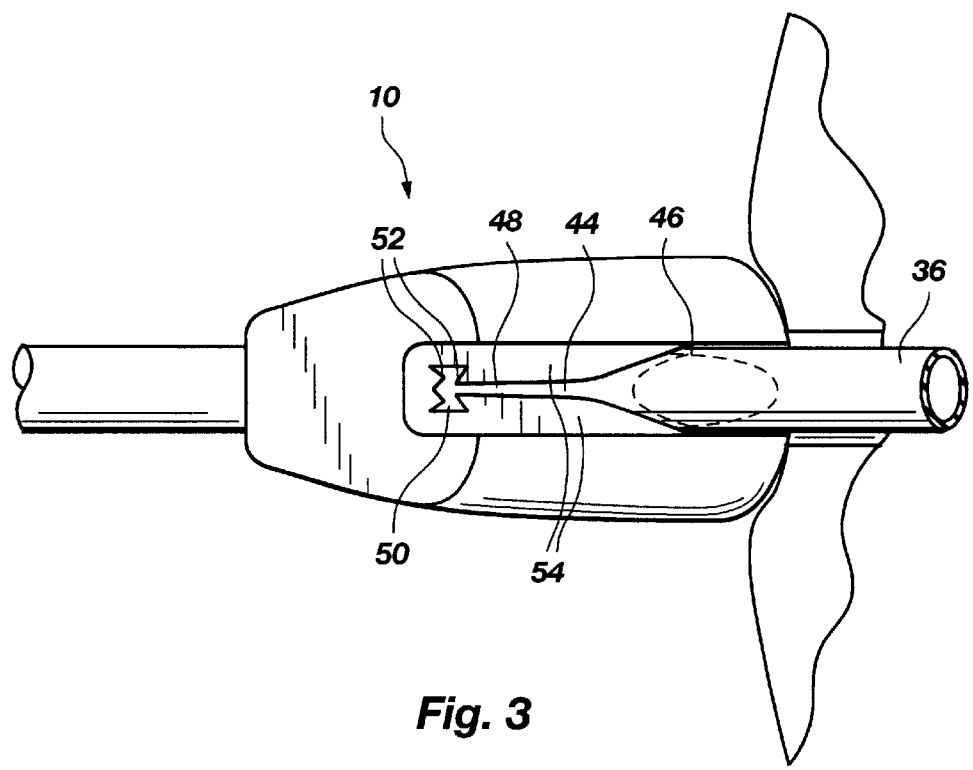
FIG. 3 is an enlarged top view of a sheath lock illustrating one lock box embodiment.
Figure 4:
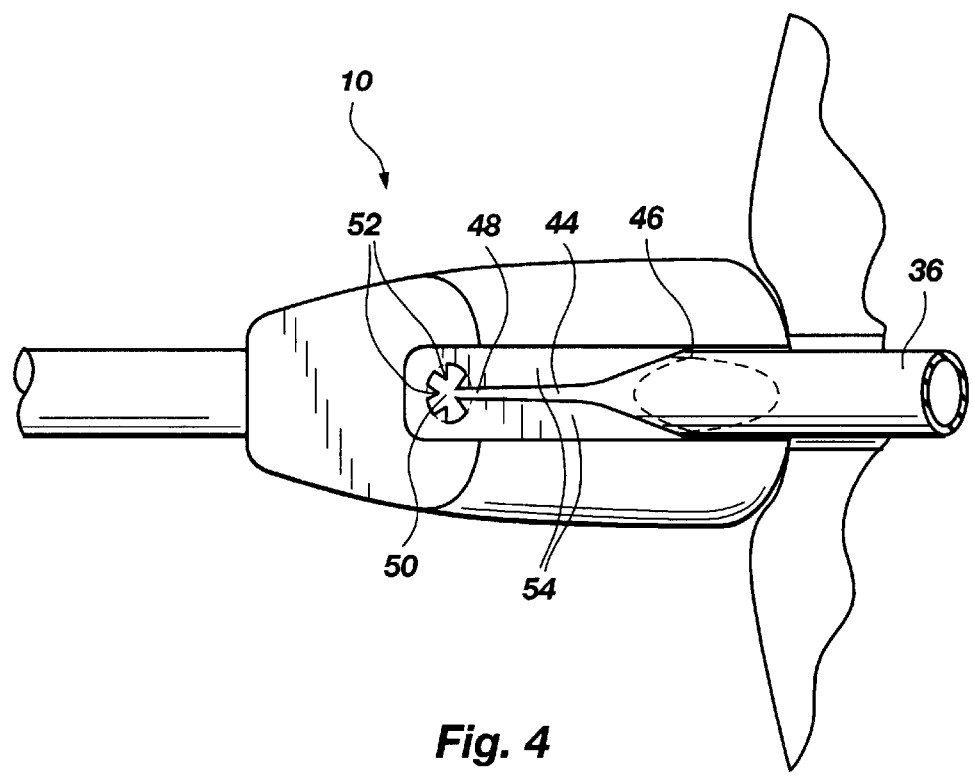
FIG. 4 is an enlarged top view of a sheath lock illustrating another lock box embodiment.

Referring to FIGS. 3 and 4, the sheath lock 10 apparatus includes a tapered slot 44 extending from a wide untapered end 46 to a narrow tapered end 48. A lock box 50 is located adjacent the narrow tapered end 48 of the tapered slot 44. The lock box 50 has a plurality of tines 52 which grip and retain the sheath 36 when it is positioned within the lock box 50.

In use, the sheath 36 passes through the tapered slot 44. The sheath 36 can freely move when located at the wide untapered end 46, but the sheath is securely locked when it is moved through the tapered slot 44 from the untapered end 46 into the lock box 50.

In a preferred embodiment, the tapered slot 44 is formed from two tapered wall sections 54 which, at the narrow tapered end 48, form two tines 52 projecting into the lock box 50. The plurality of tines 52 can be arranged in various configurations to form the lock box 50. For instance, the tines 52 can be arranged in an elliptical or circular configuration around the lock box 50, as shown in FIG. 4. Alternatively, the plurality of tines 52 can be arranged in a rectangular or square configuration around the lock box 50, as shown in FIG. 3. It will be appreciated that other means for gripping the sheath can be used, including a simple press fit configuration.

In operation, the wings 32 of the catheter inserter 16 are pinched together. This places sufficient force on the catheter 14 and needle 24 to hold them in place during venipuncture. Once blood vessel penetration is made, the distal end 18 of the catheter 14 is also inserted into the subject blood vessel. At this point, the needle 24 can be withdrawn by pulling on the handle 28 at the proximal end of the device. The wire pulls the needle in a proximal direction through the catheter 14 until it is secured in the needle receptacle 30. The handle 28 and receptacle 30 can be removed from the hub 20.

The catheter 14 can be advanced into the blood vessel. This occurs by pulling the sheath distal end 40 as shown in FIG. 2. As the sheath 36 moves distally, the catheter 14 also moves distally into the blood vessel. At the same time, the sheath 36 is split and removed from around the catheter 14. If necessary, the catheter 14 can be repositioned proximally to avoid interfering vascular structures or to obtain the desired insertion position. Once the catheter 14 is properly positioned, the sheath 36 is locked in the sheath lock 10 by sliding it into the lock box 50. A fluid line can be attached to the hub 20 at the distal end of the device such that fluid can be introduced into the patient through the catheter 14.

Figure 5:
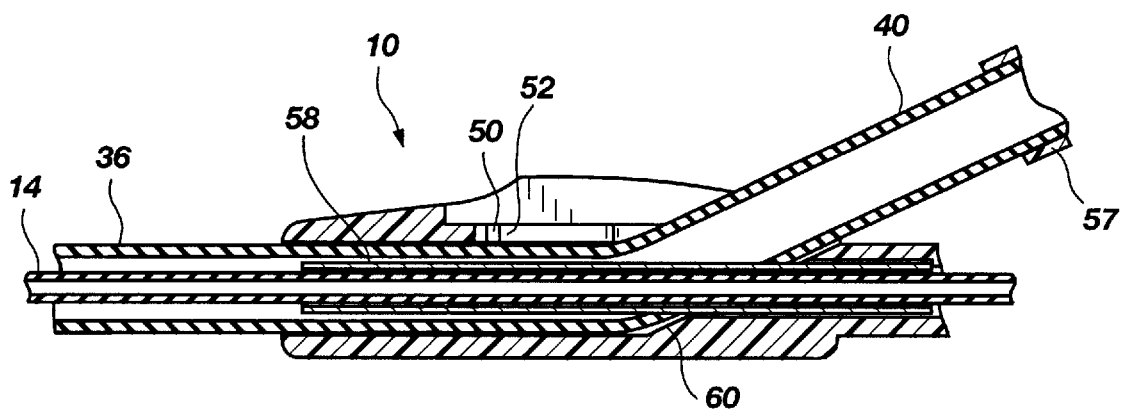
FIG. 5 is a cross-sectional view of a sheath lock showing the sheath in an un-locked configuration.
Figure 6:
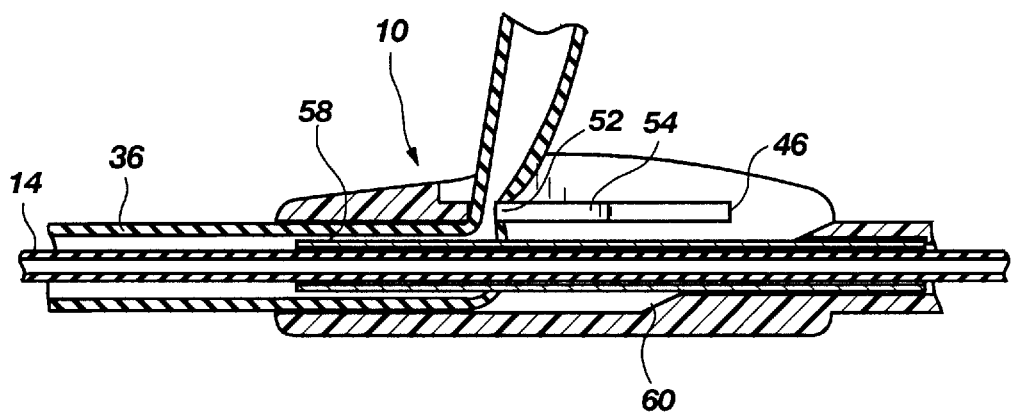
FIG. 6 is a cross-section view of the sheath lock of FIG. 5 showing the sheath in a locked configuration.

FIGS. 5 and 6 show the sheath lock 10 in cross-section. In FIG. 5, the sheath 36 is shown passing through the wide untapered end 46 of slot 44. When configured as shown in FIG. 5, the catheter 14 is advanced to a desired distance into the patient by pulling the sheath distal end 40, as shown in FIG. 2. The sheath 36 splits as it passes through the sheath lock 10. When approximately 5 cm of catheter 14 has been advanced into the patient's blood vessel, the catheter 14 is aspirated to remove any air from the system and flushed to assure patency. The catheter 14 is further advanced to a desired location. Once the catheter is properly positioned, the sheath 36 is engaged in the lock box 50 to prevent movement of the sheath and catheter 14, as shown in FIG. 6. Excess sheath 36 can be trimmed.

A proximal sheath band 56 is provided at the proximal end 38 of the sheath to prevent the catheter 14 from being advanced too far into the patient. A similar band 57 is located at the distal end 40 of the sheath 36.

FIGS. 5 and 6 also illustrate a metal sleeve 58 disposed within the sheath lock 10. Sleeve 58 is sized such that the catheter 14 fits within the sleeve 58, while the sleeve itself fits within sheath 36. The sleeve 58 protects the catheter 14 from stresses involved in splitting the sheath 36. It also aids in splitting the sheath 36. A ramp surface 60 in the sheath lock apparatus guides the sheath distal end 40 out of the sheath lock 10. The ramp surface 60 helps separate the split sheath 36 from the catheter 14.

It will be appreciated that the present invention provides a simple, yet effective sheath lock which allows the sheath to be easily pulled to properly position the catheter and also allows the sheath to be securely locked into any such desired position. The sheath lock disclosed herein is a one-piece lock, meaning that it does not require two separate lock pieces to be connected together to secure the sheath. The sheath lock permits accurate placement of a catheter within a patient, and once suitable catheter placement is obtained, the sheath lock securely maintains the catheter placement.

The present invention may be embodied in other specific forms without departing from its essential characteristics. The described embodiments are to be considered in all respects only as illustrative and not restrictive. The scope of the invention is, therefore, indicated by the appended claims rather than by the foregoing description.

What is claimed is:

1. A sheath lock for use with a splittable sheath associated with a catheter introducer comprising:
   a main body portion defining a passage extending axially therethrough and having a proximal opening and a distal opening to allow a tubular member to pass through the main body portion from the proximal opening through the distal opening;
   a tapered slot separate from the proximal opening and the distal opening in communication with the passage and extending from a wide untapered end to a narrow tapered end, such that the sheath can pass through the main body portion from the proximal opening through the tapered slot; and
   a lock box located adjacent the narrow tapered end of the tapered slot configured to grip and retain the sheath when the sheath is positioned within the lock box wherein the tapered slot is formed from two tapered wall sections which form at least one tine projecting into the lock box.

2. A sheath lock for use with a splittable sheath associated with a catheter introducer comprising:
   a main body portion defining a passage extending axially therethrough and having a proximal opening and a distal opening to allow a tubular member to pass through the main body portion from the proximal opening through the distal opening;
   a tapered slot separate from the proximal opening and the distal opening in communication with the passage and extending from a wide untapered end to a narrow tapered end, such that the sheath can pass through the main body portion from the proximal opening through the tapered slot; and
   a lock box located adjacent the narrow tapered end of the tapered slot configured to grip and retain the sheath when the sheath is positioned within the lock box, wherein the lock box comprises at least one tine for gripping and retaining the sheath.

3. A sheath lock according to claim 2, wherein the lock box comprises a plurality of the tines arranged in an elliptical or circular configuration around the lock box.

4. A sheath lock according to claim 2, wherein the lock box comprises a plurality of tines arranged in a rectangular or square configuration around the lock box.

5. A catheter introducer assembly comprising:
   a catheter having a distal end configured to be inserted into a blood vessel and a proximal end;
   a catheter introducer configured to introduce the catheter into the blood vessel;
   a splittable sheath surrounding the catheter from the catheter proximal end to the catheter introducer, said sheath having a proximal end connected to the catheter proximal end and a distal end;
   a sheath splitter configured to split the sheath and to advance the catheter through the catheter introducer as the sheath is pulled through said sheath splitter; and
   a sheath lock associated with the catheter introducer comprising:
      a main body portion defining a passage extending axially therethrough and having a proximal opening and a distal opening to allow a tubular member to pass through the main body portion from the proximal opening through the distal opening;
      a tapered slot separate from the proximal opening and the distal opening in communication with the passage and extending from a wide untapered end to a narrow tapered end, such that the sheath passes through the main body portion from the proximal opening through the tapered slot; and
      a lock box located adjacent the narrow tapered end of the tapered slot configured to grip and retain the sheath when the sheath is positioned within the lock box, wherein the tapered slot is formed from two tapered wall sections which form at least one tine projecting into the lock box.

6. A catheter introducer assembly according to claim 5, wherein the lock box comprises a plurality of tines for gripping and retaining the sheath.

7. A catheter introducer assembly according to claim 6, wherein the plurality of tines are arranged in an elliptical or circular configuration around the lock box.

8. A catheter introducer assembly according to claim 6, wherein the plurality of tines are arranged in a rectangular or square configuration around the lock box.

9. A catheter introducer assembly according to claim 5, further comprising an insertion needle disposed within the catheter to facilitate piercing a patient's blood vessel.

10. A catheter introducer assembly according to claim 9, wherein the catheter introducer comprises a pair of bendable wings which, when folded together, securely grip the catheter and needle.

11. A catheter introducer assembly according to claim 9, wherein the sheath lock further comprises a rigid sleeve partially disposed within the splittable sheath, said sleeve being sized and configured to permit the catheter to pass therethrough.

12. A catheter introducer assembly according to claim 5, wherein the splittable sheath contains means, disposed at the distal end of the sheath, for preventing the distal end of the sheath from passing through the sheath lock.

13. A catheter introducer assembly according to claim 12, wherein the means for preventing the distal end of the sheath from passing through the sheath lock comprises a band affixed to the distal end of the sheath.

* * * * *